US012625131B2

(12) United States Patent
Taagaard et al.

(10) Patent No.: US 12,625,131 B2
(45) Date of Patent: May 12, 2026

(54) METHOD OF DETECTING PRESENCE OR ABSENCE OF A CLOT IN A LIQUID SAMPLE ANALYZER

(71) Applicant: Radiometer Medical ApS, Brønshøj (DK)

(72) Inventors: Michael Taagaard, Hoersholm (DK); Peter Aage Frischauf, Broendby (DK); Flemming Aas, Dyssegaard (DK)

(73) Assignee: RADIOMETER MEDICAL ApS, Brønshøj (DK)

( * ) Notice: Subject to any disclaimer, the term of this patent is extended or adjusted under 35 U.S.C. 154(b) by 1177 days.

(21) Appl. No.: 17/500,503

(22) Filed: Oct. 13, 2021

(65) Prior Publication Data

US 2022/0042972 A1 Feb. 10, 2022

Related U.S. Application Data

(63) Continuation of application No. 16/064,742, filed as application No. PCT/EP2016/081643 on Dec. 19, 2016, now Pat. No. 11,169,141.

(30) Foreign Application Priority Data

Dec. 22, 2015 (DK) ........................... PA 2015 00831

(51) Int. Cl.
*G01N 33/49* (2006.01)
*A61B 5/145* (2006.01)
(Continued)

(52) U.S. Cl.
CPC ....... *G01N 33/4905* (2013.01); *A61B 5/1495* (2013.01); *G01N 33/4915* (2013.01);
(Continued)

(58) Field of Classification Search
None
See application file for complete search history.

(56) References Cited

U.S. PATENT DOCUMENTS

| | | | |
|---|---|---|---|
| 5,571,396 A | 11/1996 | Cormier et al. | |
| 2003/0132125 A1* | 7/2003 | Wayment | ........... G01N 33/6887 |
| | | | 205/792 |
| 2004/0033611 A1* | 2/2004 | Lundsgaard | ......... G01N 35/025 |
| | | | 436/43 |
| 2011/0312002 A1 | 12/2011 | Taktak et al. | |

(Continued)

FOREIGN PATENT DOCUMENTS

| | | |
|---|---|---|
| CN | 101596469 A | 12/2009 |
| CN | 103543278 A | 1/2014 |

(Continued)

OTHER PUBLICATIONS

International Search Report for International Application No. PCT/EP2016/081643, Mar. 1, 2017.
(Continued)

*Primary Examiner* — Elizabeth A Robinson
*Assistant Examiner* — Brittany I Fisher
(74) *Attorney, Agent, or Firm* — FBT Gibbons LLP

(57) ABSTRACT

The disclosure relates to a method of detecting a clot in a measurement chamber of a liquid sample analyzer, wherein the liquid sample analyzer comprises at least two analyte sensors, a first analyte sensor, for measuring a first analyte in a liquid sample, and one or more second analyte sensors, for measuring one or more second analytes in the liquid sample in the measurement chamber, the method comprising the steps of, (a) at least partly filling the measurement chamber with a known solution having a composition comprising the first analyte at a pre-determined level, and the second one or more analytes at pre-determined levels, (b) obtaining a first sequence of measurement results by the first analyte sensor, and simultaneously obtaining a second sequence of measurement results by the second, one or more analyte sensors, (c) determining a change of the first (Continued)

sequence of measurement results, (d) determining a change of the second or more sequence of measurement results, and (e) comparing the change of the first sequence of measurement results with the second sequence of measurement results.

20 Claims, 3 Drawing Sheets

(51) Int. Cl.
      *A61B 5/1495*      (2006.01)
      *G01N 27/327*      (2006.01)
      *G01N 33/00*      (2006.01)

(52) U.S. Cl.
      CPC ........ *G01N 33/492* (2013.01); *A61B 5/14532*
      (2013.01); *A61B 5/14539* (2013.01); *A61B*
      *5/14542* (2013.01); *A61B 5/14546* (2013.01);
      *G01N 27/3271* (2013.01); *G01N 33/0006*
      (2013.01); *G01N 33/4925* (2013.01)

(56)                References Cited

U.S. PATENT DOCUMENTS

| | | | |
|---|---|---|---|
| 2012/0090993 | A1 | 4/2012 | Mansouri et al. |
| 2013/0292246 | A1 | 11/2013 | Zelin et al. |
| 2014/0221911 | A1 | 8/2014 | Van Wieren et al. |
| 2015/0305681 | A1 | 10/2015 | Nadkarni |

FOREIGN PATENT DOCUMENTS

| | | | | | |
|---|---|---|---|---|---|
| EP | | 1906178 | A1 | 4/2008 | |
| EP | | 2275808 | A2 | 1/2011 | |
| JP | | 9-265318 | | 10/1997 | |
| JP | | 2002-214185 | | 7/2002 | |
| JP | | 2003-525450 | | 8/2003 | |
| JP | | 2005-501252 | | 1/2005 | |
| JP | | 2015-522153 | | 8/2015 | |
| WO | WO 2014/006406 | A1 | | 1/2014 | |
| WO | WO-2015143259 | A1 * | 9/2015 | ......... A61B 10/0012 | |

OTHER PUBLICATIONS

Written Opinion of the International Search Authority of International Application No. PCT/EP2016/081643.

* cited by examiner

METHOD OF DETECTING PRESENCE OR ABSENCE OF A CLOT IN A LIQUID SAMPLE ANALYZER

This application is a continuation of U.S. patent application Ser. No. 16/064,742, filed Jun. 21, 2018, which is a national stage filing under 35 U.S.C. § 371 of International Application No. PCT/EP2016/081643, filed on Dec. 19, 2016, which claims priority of Danish Patent Application No. PA 2015 00831, filed Dec. 22, 2015. The contents of these applications are each incorporated herein by reference.

The present invention relates in one aspect to a method of detecting a clot in a liquid sample analyzer comprising one or more analyte sensors for measuring a physical parameter for respective analytes, and to a liquid sample analyzer comprising a measuring chamber with one or more such analyte sensors, and a signal processor configured for detecting a clot in the measuring chamber.

In a particular aspect, the present invention relates to a method of detecting a clot in a blood analyzer comprising one or more analyte sensors for measuring blood parameters, and to a blood analyzer comprising a measuring chamber with one or more such analyte sensors, and a signal processor configured for detecting a clot in the measuring chamber.

According to a yet further aspect, a computer-implemented method of detecting a clot in a liquid sample analyzer, and a corresponding software product that can be loaded into a signal processor of a liquid sample analyzer are provided. Also in this aspect, the liquid sample analyzer may be a blood analyzer for analyzing e.g. a whole blood sample.

BACKGROUND OF THE INVENTION

Analyzers for measuring physical parameters of analytes in a liquid sample by means of respective analyte sensors are widely used in various industries, such as food industry, environmental industry, as well as medical and clinical industry. To ensure both accurate and precise results, the performance of such analyzers and the associated sensors is continuously scrutinized. This typically includes both detailed calibration and quality control procedures using standardized reference liquids including the respective analytes in well-defined compositions. The accurate and precise operation of analyzer systems is of particular importance in clinical analysis applications for analyzing physical parameters of analytes in bodily fluids, such as whole blood. In addition to the accuracy, precision, and reliability requirements, such analyzer systems for clinical applications are also subject to further critical constraints, such as a short time to obtaining a measurement result, and the capability of providing the highly reliable results from very small sample volumes.

The combination of all these constraints is particularly relevant in blood analyzers. Blood analyzers provide measurements of various parameters for analyzing the blood of a mammal subject, e.g. for establishing and/or monitoring a biological condition of the subject. Typically, the mammal subject is a human patient. In a variety of instances it is desirable to measure e.g. the partial pressure of blood gasses in a whole blood sample of the mammal subject, concentrations of electrolytes and metabolites in the blood sample, as well as the hematocrit value of the blood sample. For example, measuring pCO2, pO2, pH, Na+, K+, Ca2+, Cl−, glucose, lactate and hemoglobin values are primary clinical indications in assessing the condition of a medical patient. A number of different analyzers currently exist for making such measurements. Such analyzers are able to perform precise measurements in order to provide the most meaningful diagnostic information.

In order to use as little of the patient's blood as possible in each analysis performed, the measuring chamber which is employed to analyze a blood sample is preferably relatively small. Performing blood analysis using a small blood sample is important when a relatively large number of samples must be taken in a relatively short amount of time or if the volume of blood is limited, as in neonates. For example, patients in intensive care require a sampling frequency of 15-20 per day for blood gas and clinical chemistry measurements, leading to a potentially large loss of blood during patient assessment. Furthermore, in order to limit the number of tests which must be performed it is desirable to gather as much information as possible upon completion of each test. Furthermore, for the same reasons, it is important that the measurements and corresponding analysis results obtained from these measurements are reliable. Each measurement is therefore typically subject to a calibration and/or quality control procedure using different rinsing, calibration and/or reference liquids and the measurement chamber is thoroughly rinsed after each measurement to avoid contamination of any subsequent measurements.

However, a common issue in blood analyzers, in particular in systems with very small measurement chambers, is due to the presence of clots in whole blood samples. The clots may result in the formation of plugs impeding, obstructing or even completely blocking the fluid passages of the measurement chamber. Such clots may severely affect the measurements or even cause damage to the measurement chamber/sensor assembly. Known systems may therefore monitor the filling and discharge procedures for abnormalities in order to e.g. generate an alarm, stop the fluid handling infrastructure from feeding further fluid to the measurement chamber, and requesting a rinse and/or initiating an automated rinsing procedure. For example, the filling of the measurement chamber may be monitored by liquid sensors for detecting the passage of a liquid interface at an inlet upstream of the measurement and the corresponding subsequent occurrence of the liquid at an outlet downstream of the measurement chamber after an expected filling time. Unexpected behavior, e.g. expiry of the expected filling time without positive detection of the liquid interface at the outlet liquid sensor, may result in an alarm and/or initiation of a rinsing/maintenance procedure. Furthermore, by designing a simple flow path through the measurement chamber the formation of deposits can be counteracted and rinsing/washout can be facilitated.

While such strategies for detecting the presence of a clot in the measurement chamber are implemented and proof to be most helpful for a reliable operation of blood analyzer systems, it has been observed by the inventors that not all artifacts may be accounted for by these strategies and detection techniques.

Accordingly, it is a merit of the present invention to identify that further artifacts may arise due to clots, which are normally not detectable by the known clot detection routines that are based on e.g. flow behavior. Clots that do not noticeably affect the filling and discharge flow in the measurement chamber may nevertheless cause a severe distortion of the physical parameters of at least some of the analytes for a given sample, thus leading to erroneous analysis results. Therefore, there is a need for rapidly and reliably detecting any such additional causes of potential artifacts in blood analyzers in order to ensure accuracy and precision of the measurements and avoid the waste of valuable patient blood. Furthermore, such additional artifacts may also occur more generally in liquid sample analyzers. Accordingly, there is a further need for rapidly and reliably detecting any such additional causes of potential artifacts in liquid sample analyzers in order to ensure accuracy and precision of the measurements.

Object of the present invention is therefore to provide a method of detecting a clot contamination in a measurement chamber with improved sensitivity, and a system adapted to perform such clot detection method with improved sensitivity.

SUMMARY OF THE INVENTION

A first aspect of the invention relates to a method of detecting a clot in a measurement chamber of a liquid sample analyzer, wherein the liquid sample analyzer comprises a first analyte sensor and one or more second analyte sensors, wherein each of the first and second analyte sensors are arranged for measuring a physical parameter for a respective analyte in a liquid sample in the measurement chamber, the method comprising the steps of: (a) at least partly filling the measurement chamber with a known solution having a composition comprising the respective analytes at a pre-determined level; (b) obtaining a first time sequence of measurement values by the first analyte sensor; (c) obtaining a respective second time sequence of measurement values by each of the one or more second analyte sensors; (d) determining an actual change of measurement values over time from the obtained first time sequence; (e) comparing the actual change with an expected change of said measurement values over time, wherein the expected change is developed from at least the ensemble of second time sequences of measurement values or a subset thereof; and (f) determining presence or absence of a clot in the measurement chamber based on said comparison.

The present invention is useful for the detection of clots in the measurement chamber of a liquid sample analyzer. The detection result may be used as a part of the self-control routines, may be requested by a user or otherwise be triggered externally; The detection result may further trigger an alarm or error state of the liquid sample analyzer, and may also be used to invoke a clot removal procedure and/or request external service, maintenance or replacement of the faulty measurement chamber if removal of the clot proofs unsuccessful.

A clot of the kind that becomes detectable by the present invention spoils the measurement by polluting the sample inside the measurement chamber. It should be noted that this is of particular relevance to liquid sample analyzers with very small sample volumes that are particularly susceptible to pollution, due to even minute amounts of parasitic analyte emitted from a clot, or due to minute amounts of actual analyte removed from the actual sample by absorption in the clot. The clot may be seen as a reservoir with a capacity for the uptake and emission of analyte, thereby causing pollution by acting as an analyte source or as an analyte sink whenever there is a gradient in the analyte concentration between the clot and the surrounding liquid sample.

A liquid sample analyzer may typically comprise a measurement chamber, one or more analyte sensors facing the measurement chamber, an analyzer part with a signal processor, and fluid handling infrastructure. The measurement chamber is adapted for receiving and containing a liquid sample to be analyzed with respect to a number of different analytes. The sensor surfaces facing the measurement chamber are selectively sensitive to respective analytes and are adapted to generate corresponding signals. The signal processor communicates with the sensors for collecting and processing the signals. In "normal" operation, the user may provide a liquid sample at an input port of the analyzer. The liquid sample is transferred to the measurement chamber comprising the sensors. The measurement chamber may be equipped with a plurality of analyte sensors arranged to provide essentially simultaneous measurements on analyte parameters in a liquid sample, e.g. a whole blood sample, wherein preferably the required sample amount for obtaining precise and reliable data is as small as possible. A detailed example of a sensor assembly design that is particularly suitable for simultaneously measuring a plurality of different parameters in bodily fluids, particularly in whole blood, and its use in a blood analyzer is e.g. found in the European patent EP 2 147 307 B1. Details of a suitable sensor design that may be used for blood and body fluid parameter analysis in a liquid sample analyzer are also found in literature. For example, EP 2 361 380 B1 discloses a planar sensor determining the partial pressure of $CO_2$ of a blood sample, and U.S. Pat. No. 6,805,781 B2 discloses a sensor with an ion-selective electrode device using a solid state, inner reference system.

When using solid state sensors, it is not known how the sensor characteristic develops over time as there is no fixed reference for the sensor. It is thus impossible to predict how the sensor should behave under certain circumstances. It is therefore a part of the invention, that the sensor development is compared to an expected development, where the expected development is a second sensor from the same batch of sensors. The second sensor is similar to the first sensor but may be measuring a different parameter. One can then expect that the two sensors will change in the same way over time. Hence the expected change is a linear regression of the measurement results of the second sensor, and the actual change is the linear regression of the measurements results of the first sensor. If the line regression curve of the first sensor differs from the linear regression curve of the comparable second sensor, there must be something, e.g. a kind of pollution affecting one of the two sensors. When only comparing two sensors, it is not possible to know which one of the two sensors is affected. If however three or more sensors are used for developing the expected change, it may be determined which sensor is affected, as that sensor will develop different from the other sensors.

Following pre-programmed routines, measurements are performed using the analyte sensors. In order to obtain a time sequence of measurement values from an analyte sensor for the respective analyte, a series of values attributable to the physical parameter measured by the sensor is recorded subsequently one after the other at respective times. Determining a change from the first time sequence may include calculating a slope from the time sequence, e.g. by a linear regression. Developing the expected change from the one or more second time sequences may e.g. include determining a change for each of the second sequences, and determining the expected change as an average of the changes of the second sequences. The average of changes used for determining the expected change may in addition to all the second time sequences also include the first time sequence, or, alternatively be restricted to a particular subset of the recorded first and second time series. The analyte sensors generate signals representative of a physical parameter for the respective analyte and provide the signals to the analyzer part. The analyzer part comprises a signal processor that is adapted to receive and process signals from the analyte sensors, and present the processed signals as output to a user or to a subsequent/further data analysis. After measurement, the liquid sample is discharged, and the measurement chamber is prepared for the next measurement. Performing the measurements, calibration tasks, and quality control procedures thus typically involves the loading, unloading, rinsing, cleaning and re-loading of different liquids, which may be done by the fluid handling infrastructure. Fluid handling may be manual, partly automated or fully automated depending on the system. The fluid handling infrastructure may comprise a kit with process solutions of known compositions. Advantageously, the signal processor may further be adapted to communicate with the fluid handling infrastructure for controlling fluid flow to and from the measurement chamber, e.g. for filling, flushing or discharging a user sample and any of the process solutions in an automated or at least semi-automated manner. The analyzer may perform self-control routines including calibration and quality control. An example of a method for performing calibration and quality control of a sensor in a liquid sample analyzer in a cyclic manner is described for example in U.S. Pat. No. 7,338,802 B2. Most advantageously, the analyzer is further programed to maintain the measurement chamber and the associated sensors in a well-defined electrochemical idle state and to continuously monitor the status of the analyzer in general and of the sensor status in particular. If any abnormality is detected, the analyzer may indicate the deviation to a user, and may further initiate measures or indicate ways of overcoming an error state.

An important and distinguishing advantage is that the present invention uses actual analyte measurements performed inside the measurement chamber to detect a clot. In fact, the invention may most advantageously be performed using signals from the very analyte sensors that would be affected by the presence of a clot in the measurement chamber. The high reliability of the clot detection according to the present invention is amongst others achieved, due to the fact that the presence of a clot is determined directly from the characteristics of the mechanism, which is the root cause of the artefacts that the clot would also introduce in a measurement on a valuable user sample. Furthermore, the method is to be performed on a known solution, which preferably may be a process fluid generally used for calibration and quality control of the sensors. The method is therefore particularly well suited for integration with the continued self-control procedures that may be performed when the analyzer is idling.

When the analyzer is not measuring on a sample, but is in a state where it is ready to receive a user sample, the sensor board comprising the different sensors is usually loaded with a rinse solution containing the different analytes on which the analyzer measures. During this idle state, the analyzer is measuring the analytes within the rinse solution at intervals of e.g. 1 minute; this is used for calibrating the analyzer. By frequently calibrating the analyzer it is ensured that the analyzer is always ready for measuring a user blood sample, as it has been calibrated within the last minute. However leaving a rinse solution in the measurement chamber for longer periods of time allows the clot time for uptake of analytes which is a following measurement on a blood sample may pollute the measurement, as the blood sample is only in the measurement chamber for a short period of time. A sensor covered by a clot will therefore only see the clot containing rinse and since the exchange between the clot and the blood sample is very slow due to diffusion rates being small, the sensor will not be able to actually see the blood sample within a measuring cycle, i.e. before the sample is discarded to waste. As the measurements taken on rinse during idling is used for calibration, the proposed solution ensures that the analyzer is always calibrated correctly.

After a measurement on a blood sample the measurement chamber is cleaned by flushing it with a rinse solution interrupted by air bubbles which creates several waves of liquid which is very effective for cleaning. After cleaning the measurement chamber is filled with a rinse or calibration solution on which the analyzer measures at frequent intervals e.g. every minute. After about 10 minutes of measuring the effect of a clot often starts to show as the clot will start to act more like the rinse or calibration solution in the measurement chamber due to equilibrium between the clot and the rinse solution in the chamber, i.e. the clot starts to look like rinse for the sensor after about 10 minutes time.

The clot detection system accumulates the measurements results for every minute for the first 5 minutes, that the system is in operation. After the first five minutes, the system still only look at the last five measurement results, for every minute a new result gets recorded and the oldest result is discarded from the recording.

In an embodiment of the invention the system detects clots merely by looking at discrete values, i.e. comparing the measurement result on rinse of the first analyte sensor with the measurement result of the second analyte sensor, and if the difference between the two results exceed a threshold value, a clot is present in the measurement chamber, and a clot removal procedure is initiated.

Every two hours the analyzer is calibrated using a two point calibration using the rinse solution as a first calibration point and a second solution having analytes at higher concentrations as a second calibration point. When the analyzer reached the two hour point, the clot detection system is reset and the system starts over. Furthermore, by monitoring the status of an ensemble of first and one or more second analyte sensors, and comparing/referring the status of each of the individual analyte sensors to the collective behavior, an abnormal behavior may be detected with a surprisingly high precision and reliability, even in a configuration where the sensors are subject to a substantial offset drift exceeding a clinically acceptable level of signal variance by orders of magnitude. The abnormal behavior may also be detected in an environment, where such drift events are unknown beforehand, and are impossible to predict, at least with sufficient precision as required to be able to distinguish the presence of a clot that would affect the measurement from other sources of incertitude. The present invention is therefore particularly useful for cases where the multiple sensors of a liquid sample analyzer are subject to unpredictable, but collective drift.

The same and further advantages are also achieved by the further embodiments and the further aspects of the invention as defined in the following.

Further according to one embodiment of the method, the expected change is developed from an ensemble including the first time sequence of measurement values. Thereby, the expected change may be based on a larger number of measurement values. Alternatively, the measurement values obtained for the first analyte sensor, i.e. the sensor that is checked for a deviation from the expected behavior is excluded from the average.

Further according to one embodiment of the method, developing the expected change includes calculating an average sequence of measurement values from the first and/or second sequences of measurement values.

Further according to one embodiment of the method, the actual change and the expected change are determined as rates of change.

Further according to one embodiment of the method, presence of a clot is determined if the difference between the actual change and the expected change is above a threshold. This allows for a simple implementation of the discrimination criterion for determining presence of a clot that would cause artefacts significantly affecting the measurement results on a user sample. The threshold may be determined in any suitable manner, e.g. by observing over a longer period of operation a "normal" behavior, where the measurement chamber is clearly free of clots affecting the accuracy and precision of the analysis results and deriving a threshold from that observation. As further discussed below, such a series of normal behavior is e.g. shown in FIG. 3. According to some embodiments, the variation of the signal under normal idling behavior may be attributed with a characteristic value, e.g. a peak-peak amplitude, or described statistically by a standard deviation, a two-sigma variation, or the like. Based on the characteristic value for the variation of the idle signal under normal operation conditions, a threshold value may be derived. For example a threshold of two or three times the characteristic value may be selected. Presence of a clot may be determined, if only one of the analyte sensors exceeds a respective threshold, thereby indicating an abnormal behavior.

Further according to one embodiment of the method, absence of a clot is determined if the difference between the actual change and the expected change is below a threshold. This criterion of determining absence of a clot is complementary to the above criterion for determining presence of a clot. Correspondingly, this criterion allows for a simple implementation of the discrimination criterion. The threshold may be determined in any suitable manner, e.g. as described above. Absence of a clot may be determined, e.g. if all of the analyte sensors included in the detection procedure stay below their respective threshold, thereby indicating a normal behavior. The thresholds may be predetermined, with respective values for each of the analyte sensors. Preferably, for the sake of simplicity, a common threshold value that is the same for all analyte sensors is determined. Further preferably, the common threshold value or the respective threshold values are the same for determining presence and absence of a clot to avoid potential ambiguities.

Further according to one embodiment of the method the first and second analyte sensors are located at different locations along the measurement chamber. By including measurements in the clot detection procedure that have been obtained from sensors that are spaced apart from each other, at different locations within the measurement chamber, the probability for the sensitive surfaces of the sensors to be simultaneously covered by a clot is reduced. Preferably, the different locations are distributed along a flow path from an inlet port to an outlet port of the measurement chamber over essentially the entire length of that flow path, or at least 70%, or at least 50%, or at least 30%, or between 60% and 90%, or between 40% and 60% of the length of that flow path. Thereby, it may be ensured that the detection mechanism is not even blinded by a large clot affecting all analyte sensors included in the detection procedure at the same time and in the same manner.

Further according to one embodiment of the method, the first and/or second sequences of measurements are used for maintaining a calibration of the respective analyte sensors for subsequent measurements. Thereby, an advantageous integration of the clot detection method in the existing self-control procedures and/or continued idle state reference updating procedures is achieved.

Further according to one embodiment of the method, the one or more physical parameters are one or more of the types analyte concentration, partial pressure of a gas in liquid, and pH-value. Even though the sensors measure different types of physical parameters, they may still be comparable with each other, and exhibit a collective behavior. For example, the sensors may all be electrochemical sensors of a common electrode design, such as electrode devices with a solid state, inner reference system. By including a broader range of sensor types, the versatility/applicability of the method in different measurement chamber/sensor setups is achieved. For a given measurement setup, including a broader range of sensor types has the advantage that more sensors can be included in the clot detection procedure, thereby increasing the sensitivity, stability, and/or reliability of the clot detection.

Further according to one embodiment of the method, the first and second analyte sensors are adapted to measuring the same type of physical parameters. By including only sensors adapted for measuring the same type of physical parameters, a more uniform collective drift behavior of the different sensors may be expected.

Further according to one embodiment of the method, the first and second analyte sensors are adapted to measuring the same type of physical parameters for different analytes. By including a diverse selection of sensors of the same type that are selective for different analytes, an improved versatility/applicability of the method in different measurement chamber/sensor setups is achieved, while it still may be expected that the sensors exhibit a uniform collective drift behavior. For a given measurement setup, this has the advantage that more sensors can be included in the clot detection procedure, thereby increasing the sensitivity, stability, and/or reliability of the clot detection.

Further according to one embodiment of the method, the first and second analyte sensors are electrochemical sensors, each sensor comprising an ion selective electrode. Using sensors of similar types in the clot detection procedure has the advantages as already mentioned above.

Further according to one embodiment of the method, the electrochemical sensor includes an electrode device with a solid state inner reference system. Sensors with electrode devices including a solid state reference exhibit a large reference drift that may exceed the required precision for reliably detecting pollution by a clot in the measurement chamber by orders of magnitude. However, in a given measurement chamber of a given production batch, the background drift tends to be largely the same for all electrode devices. The present invention effectively removes the collective background drift component. The present invention is therefore particularly useful in combination with sensors having a solid state inner reference system.

Further according to one embodiment of the method, the first and second analyte sensors are optical sensors. Since a clot that is present in a measurement chamber actually pollutes the liquid sample that is to be measured, any type of sensor that can be attributed an otherwise collective behavior, such as optical sensors, may be exploited to determine the presence or absence of a clot using the invention. As mentioned several times above, it is advantageous to use sensors of similar types in the clot detection procedure.

According to a further aspect of the invention, a liquid sample analyzer is provided that is adapted for performing a method of clot detection according to any of the preceding claims, the liquid sample analyzer comprising a measurement chamber with inlet and outlet ports for feeding and discharging a liquid sample to the measurement chamber, at least one analyte sensor facing the measurement chamber, the analyte sensor being arranged for measuring a physical parameter for a respective analyte in a liquid sample in the measurement chamber, and a signal processor configured for receiving signals from the analyte sensors as an input, for performing a comparison of actual and expected changes based on that input, and for determining presence or absence of a clot in the measurement chamber based on the comparison. By including a signal processor, which is configured to control the liquid sample analyzer to perform the steps for detecting a clot as described herein, the same advantages as achieved by the method according to any of the embodiments of the invention are implemented in a liquid sample analyzer.

Further according to one embodiment, the liquid sample analyzer is adapted for the measurement of blood parameters in whole blood samples. The present invention is particularly useful for implementation in a blood analyzer, where the requirements for clinically acceptable measurement precision and accuracy are extremely challenging.

Advantageously according to some embodiments, the analyte sensors are one or more of dedicated sensors for measuring a partial pressure of a gas, a concentration of an electrolyte, a concentration of one or more metabolites, a concentration of one or more nutritional substances, a concentration of one or more pharmaceutical substances, and pH.

Further advantageously according to some embodiments, the one or more analytes are one or more of $Na^+$, $K^+$, $Ca^{2+}$, $Mg^{2+}$, $Cl^-$, glucose, lactate, urea, creatinine, $CO_2$, and $O_2$.

Further according to one embodiment of the liquid sample analyzer, the first and second analyte sensors are located at different locations along the measurement chamber. By including measurements in the clot detection procedure that have been obtained from sensors that are spaced apart from each other, at different locations within the measurement chamber, the probability for the sensitive surfaces of the sensors to be simultaneously covered by a clot is reduced. The same advantageous arrangements of the sensors in the measurement chamber along the flow path from the inlet to the outlet as already mentioned above are applicable.

According to a yet further aspect of the invention, a computer-implemented method is provided for detecting a clot in a measurement chamber of a liquid sample analyzer comprising a plurality of analyte sensors, the plurality of analyte sensors each being arranged for measuring a physical parameter for a respective analyte in a liquid sample in the measurement chamber, the method comprising the steps of:

receiving a first time sequence of measurement data for a first analyte obtained by a first one of the analyte sensors on a known solution having a composition comprising the respective analytes at a predetermined level;

determining an actual change of the measurement data over time from the obtained first time sequence;

receiving respective further time sequences of measurement data for respective analytes obtained by one or more further ones of the analyte sensors on the known solution having a composition comprising the respective analytes at a predetermined level;

developing an expected change from at least the ensemble of the further time sequences or a subset thereof;

comparing the actual change with the expected change of said measurement data over time; and determining presence or absence of a clot in the measurement chamber based on the comparison.

Thereby the analogue advantages as discussed above with respect to the method and apparatus according to the invention are achieved. In addition thereto this allows implementing the method of the invention in a signal processor of a liquid sample analyzer, such as in particular a blood analyzer.

Yet according to a further aspect of the invention, a software product is provided that can be loaded to a signal processor of a liquid sample analyzer, the signal processor being configured for communicating with a plurality of analyte sensors facing a measurement chamber of the liquid analyzer, the software product comprising instructions for:

(i) collecting at least from a first one of the analyte sensors at least a first time sequence of measurement data for a first analyte obtained on a known solution having a composition comprising the first analyte at a predetermined level;

(ii) collecting respective further time sequences of measurement data for respective analytes obtained by one or more further ones of the analyte sensors on the known solution having a composition comprising the respective analytes at a predetermined level;

(iii) determining an actual change of the measurement data over time from the first time sequence;

(iv) developing the expected change from at least the ensemble of the further time sequences or a subset thereof;

(v) comparing the actual change with an expected change of said measurement values over time; and (vi) determining presence or absence of a clot in the measurement chamber based on the comparison.

The software product is useful for configuring the signal processor of a liquid sample analyzer for performing the method of determining the presence of a clot in a measurement chamber of the liquid sample analyzer comprising one or more analyte sensors, the one or more analyte sensors being arranged for measuring a physical parameter for a respective analyte in a liquid sample in the measurement chamber. The software product may even be used to upgrade existing liquid sample analyzers to include a clot detection procedure according to the invention in the toolbox of the liquid analyzer, e.g. for improving the self-control, calibration, and/or quality control procedures. By such an upgrade, an existing liquid analyzer may be improved to provide more reliable, more accurate and/or more precise measurement results. This is of particular importance for apparatus used in a clinical environment, where reliable, accurate and precise measurements are of the utmost importance, yet avoiding a costly replacement of the apparatus.

Further according to one embodiment of the software product, the signal processor is further configured for communicating with a fluid handling system adapted for feeding and discharging liquid samples to the measurement chamber of the liquid analyzer, the computer program/software product further comprising instructions for at least partially filling the measurement chamber with the known solution prior to processing instruction (i). By including fluid handling instructions in the software product, an improved automated clot detection procedure is achieved, which also allows for performing automatic measures for self-cleaning and/or clot removal in response to the determination of the presence of a clot in the measurement chamber.

BRIEF DESCRIPTION OF THE DRAWINGS

Preferred embodiments of the invention will be described in more detail in connection with the appended drawings, which show in FIG. 1 a diagram of a blood analyzer according to one embodiment, FIG. 2 a graph plotting the rate of change as a function of time for a set of three analyte sensors, the data indicating presence of a clot in the measurement chamber, and in FIG. 3 a further graph plotting the rate of change as a function of time for a further set of three analyte sensors, the data indicating absence of a clot in the measurement chamber.

DETAILED DESCRIPTION OF PREFERRED EMBODIMENTS

Figure 1:
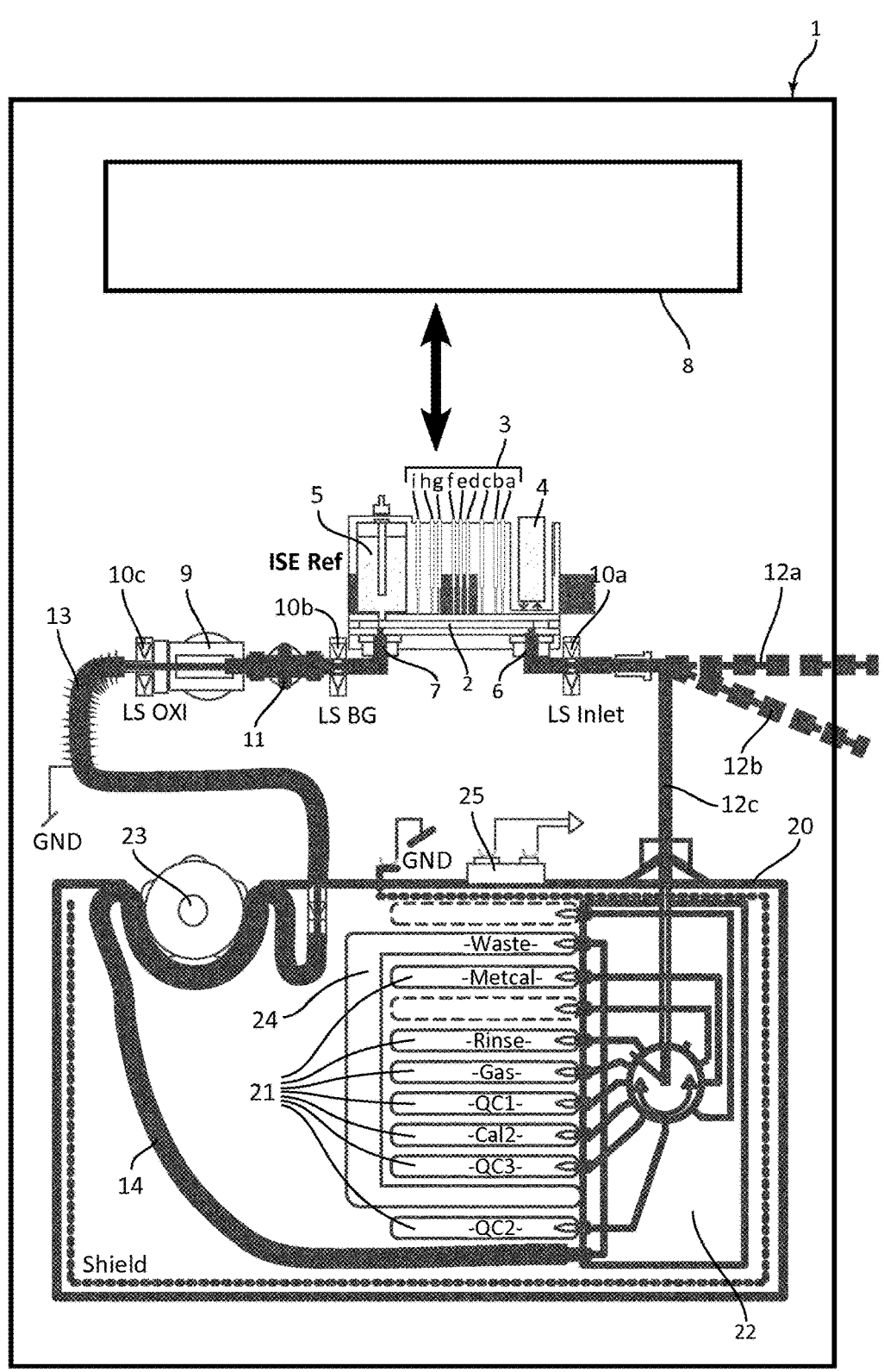

FIG. 1 shows schematically a liquid sample analyzer 1 with an analyzer part having a signal processor 8, one or more analyte sensors 3(a-i), 4, a measurement chamber 2, and fluid handling infrastructure 20. For performing measurements, the user may provide a liquid sample at an input port 12a/b of the analyzer 1. The liquid sample is transferred through an inlet port 6 to the measurement chamber 2 comprising a plurality of analyte sensors 3, 4. The analyte sensors 3, 4 are arranged to provide essentially simultaneous measurements on analyte parameters in a liquid sample, e.g. a whole blood sample. Preferably, the required sample amount for obtaining precise and reliable data is as small as possible. A detailed example of a sensor assembly design that is particularly suitable for simultaneously measuring a plurality of different parameters in bodily fluids, particularly in whole blood, and its use in a blood analyzer is e.g. found in EP 2 147 307 B1. Following pre-programmed instructions loaded in a signal processor 8 and/or user input, measurements are performed using the analyte sensors 3, 4. The analyte sensors 3, 4 generate signals that are representative of a physical parameter for the respective analyte and provide the signals to the signal processor 8 of the analyzer part. The signal processor 8 is adapted to receive and process signals from the analyte sensors 3, 4, and present the processed signals as output to a user or to a subsequent/ further data analysis. After measurement, the liquid sample is discharged, and the measurement chamber 2 is prepared for the next measurement. The embodiment of the analyzer shown in FIG. 1 is particularly adapted for the measurement of blood parameters, and further comprises an optional oximetry measurement device 9 downstream of the measurement chamber 2. Performing the measurements, calibration tasks, and quality control procedures thus typically involves the loading, unloading, rinsing, cleaning and reloading of different liquids, which may be done by the fluid handling infrastructure 20. The fluid handling may be controlled in an automated way by the signal processor 8 according to pre-programmed instructions and/or user input. The fluid handling infrastructure 20 includes a number of reservoirs 21 pre-filled with process liquids (RINSE/CAL1, CAL2, QC1, QC2, QC3) for rinsing/wash-out, calibration and quality control tasks. The process liquids (RINSE/ CAL1, CAL2, QC1, QC2, QC3) have a known composition. The exact composition of a given batch may be stored in a chip 25 that may be attached to a cassette comprising the reservoirs 21, wherein the chip 25 may be read by the signal processor 8. The process liquid (RINSE/CAL1, CAL2, QC1, QC2, QC3) for a given process step may be selected by a fluid selector valve 22, and via feed line 12c transferred through the inlet port 6 to the measurement chamber 2. Correct filling of the measurement chamber 2 may be monitored and verified by visual inspection or according to known procedures by observing the propagation of a liquid interface through the system by means of liquid sensors 10a, 10b, 10c located upstream and downstream of the measurement chamber, such as at the inlet 6 ("LS inlet" 10a), at the outlet 7 ("LS BG" 10b), and just after the oximetry measurement device 9 ("LS OXI" 10c), respectively. The fluid flow through the analyzer is driven by a pump 23, here a peristaltic hose-pump arranged downstream of the measurement chamber 2 and the oximetry measurement device 9 and connected thereto via fluid line 13. The discharged fluids are finally transported through fluid line 14 to the waste reservoir 24.

By way of example, a kit of process fluids may include the following compositions with approximate concentrations of different substances contained in these compositions as given in Table 1 below.

TABLE 1

| Substance | Unit | Concentration | | |
|---|---|---|---|---|
| | | RINSE/CAL1 S1920 | CAL2 S1930 | CAL3 S1940 |
| pH | | 7.30 | 6.8 | NA |
| pCO$_2$ | mmHg | 35 | NA | 80 |
| pO$_2$ | mmHg | 180 | NA | NA |
| cNa$^+$ | mmol/L | 150 | 70 | NA |
| cK$^+$ | mmol/L | 4 | 10 | NA |
| cCl$^-$ | mmol/L | 95 | 50 | NA |
| cCa$^{2+}$ | mmol/L | 0.5 | 2.3 | NA |
| cGlu | mmol/L | 0 | NA | 10 |
| cLac | mmol/L | 0 | NA | 10 |
| ctHb | g/dL | NA | NA | 0 |

Upon start-up and, in an ongoing manner, during uptime, the analyzer 1 performs self-control routines. If any abnormality is detected, the analyzer 1 indicates the deviation to a user, and may further indicate ways of overcoming an error state. On the other hand, when the analyzer indicates normal operation, measurements can be performed immediately. Advantageously according to some embodiments, the self-control routines may be performed during idle times, i.e. when the analyzer is in an idle state, where it is not used for performing actual measurements on a user's sample. The self-control control routines may include continued repetitive measurements performed on a calibration-grade process liquid with a precisely known composition, as e.g. stored on chip 25. A suitable liquid is for example the process liquid RINSE/CAL1, labelled S1920 in the Table 1 above. The signals obtained for each of the different analyte sensors on the well-known composition may then be used to continuously update the reference for the respective analyte measurements.

Figure 2:
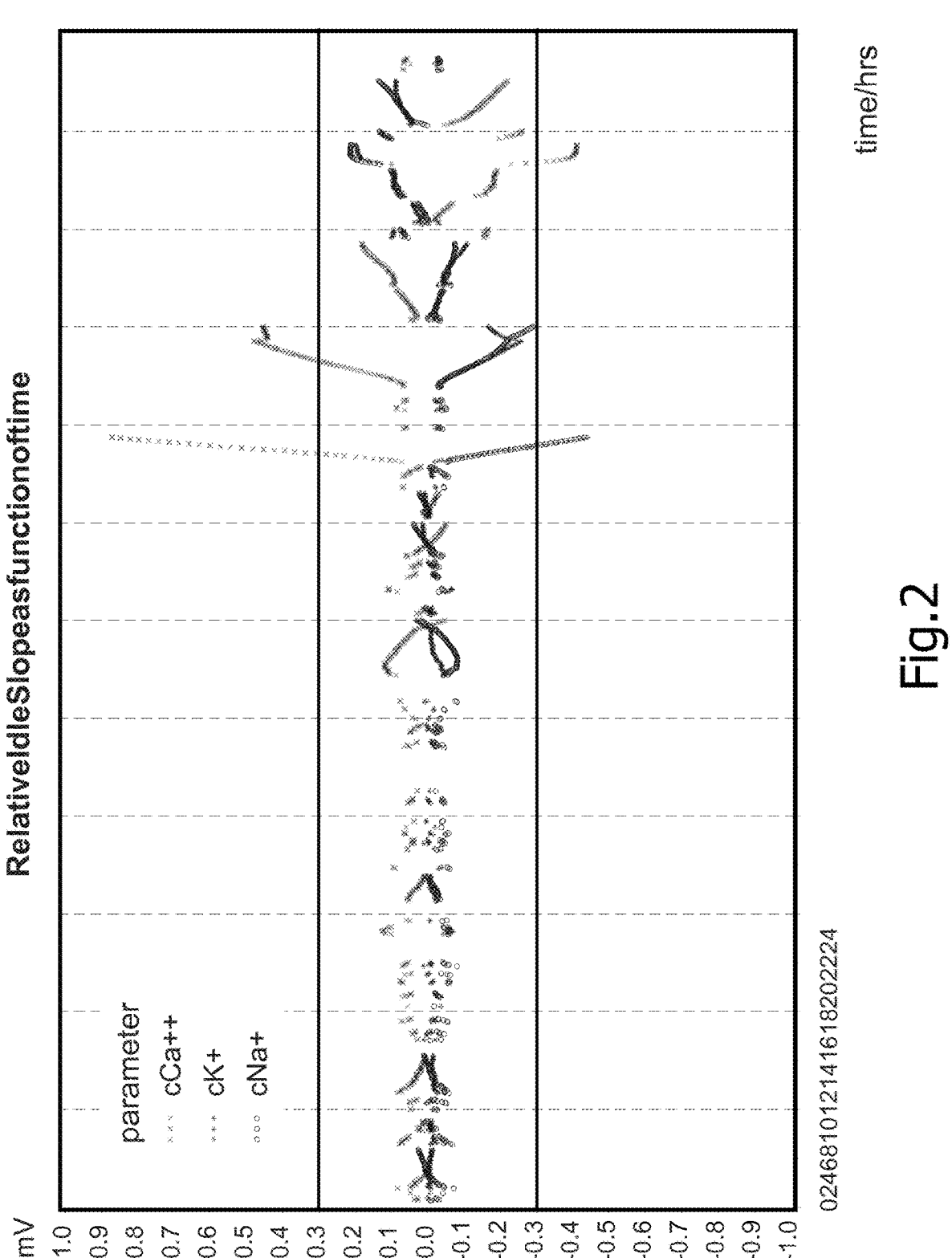
Figure 3:
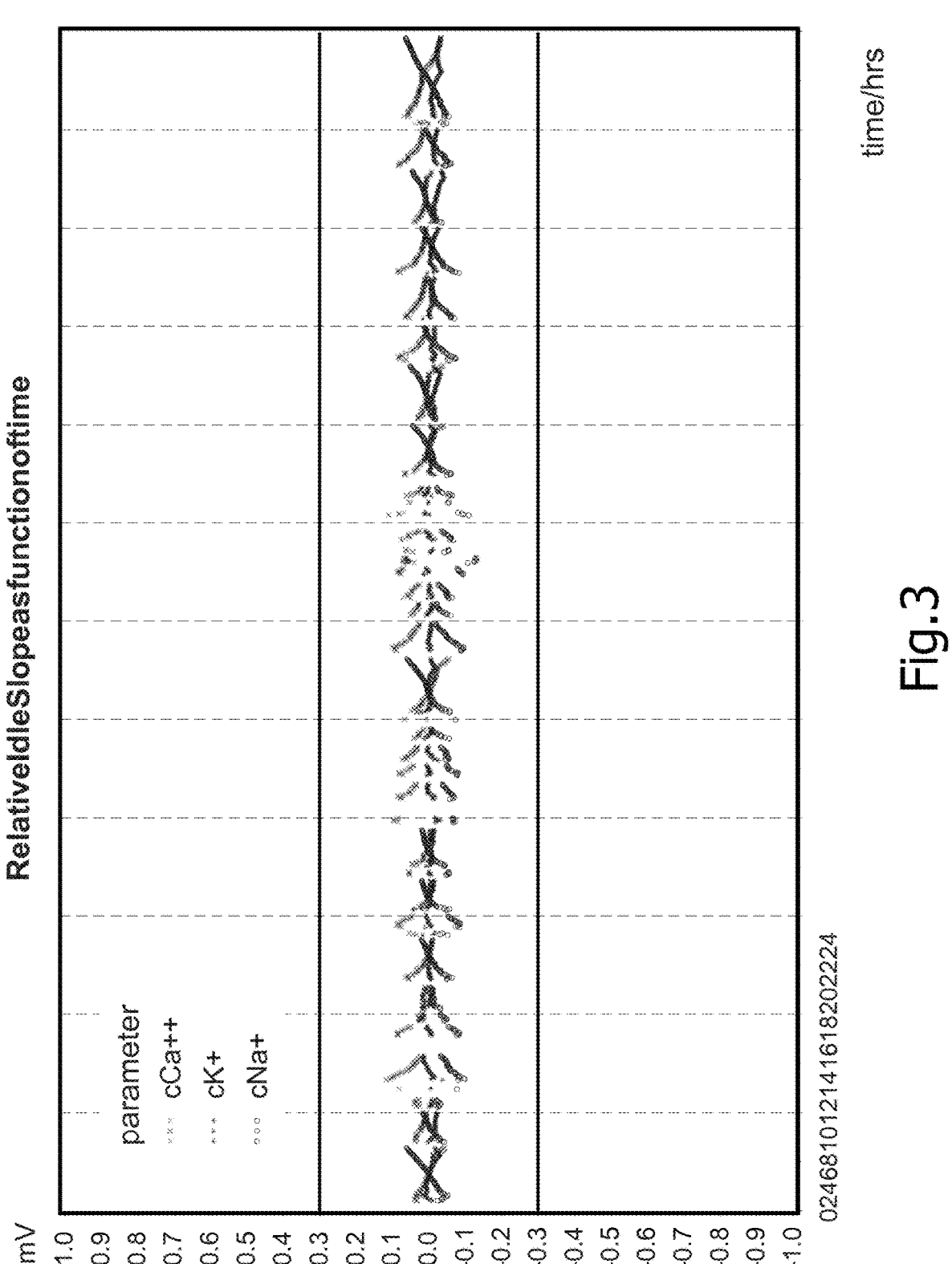

Such data from continued idle state measurements on the RINSE/CAL1 process liquid over a period of operation of 24 hrs are shown in FIGS. 2 and 3. FIGS. 2 and 3 show graphs plotting for a set of three analyte sensors a representative value that may be used as a discrimination criterion for determining presence or absence of a clot in the measurement chamber of a blood analyzer. The three sensors of FIGS. 2 and 3 are all electrochemical sensors adapted to measure concentration of Ca$^{2+}$-ions (crosses), K$^+$-ions (stars), and Na$^+$-ions (circles), respectively. In the graphs of FIGS. 2 and 3, the representative value reflecting the synchronized status of the three sensors is a relative idle slope, wherein the relative idle slope is determined from the continued idle state updating measurements described above. The relative idle slope for each electrode is here determined as the slope obtained from a regression to a time sequence of measurements for each of the analyte sensors included in the clot detection procedure, and referring the respective slope to the ensemble of all the analyte sensors included in the clot detection procedure by subtracting the average of the slopes of all said sensors. Alternatively, the average slope subtracted from the slope of a given analyte sensor may be taken over the slopes for all sensors included in the clot detection procedure, except for the given sensor.

The data in FIG. 3, and in FIG. 2 up to about 14:00 hrs, behave "normal", i.e. the data do not indicate the presence of any contaminant in the measurement chamber 2 that would significantly affect the result of a measurement on a user sample. The synchronized status slopes for the idle measurements of all three analyte sensors tend to stabilize around zero. Only small characteristic recovery decays are observed after a user's measurement, a calibration routine, or a quality control procedure has perturbed the state of the analyte sensors, until the sensor signal stabilizes again around zero.

However, between 14 hrs and 16 hrs (at about 15 hrs towards positive values) in the graph of FIG. 2, a dramatic change of the signal from the Calcium ion sensor is observed—here expressed by a dramatic increase in the relative idle slope for the $Ca^{2+}$-sensor, and a corresponding rapid decrease of the relative idle slope values for the remaining two analyte sensors. This pronounced deviation is the signature of the presence of a clot in the measurement chamber, acting as a reservoir for the delayed up-take and emission of analytes. If un-detected and if not removed, the clot may cause contamination/pollution of subsequent samples in the measurement chamber and/or distortion of the measurement values for at least some of the analytes of a given sample. In the event between 14 hrs and 16 hrs in FIG. 2, apparently the clot contributes with a delayed excessive emission of $Ca^{2+}$ into the RINSE/CAL1 solution of the idle measurement. An appropriate threshold value may be chosen as a discrimination criterion for determining the presence (or absence) of a clot. For example, in FIGS. 2 and 3, a threshold of e.g. (+/−0.3) has been defined for the deviation of the relative idle slope from its stabilized state around zero. The threshold is marked in the graph by two horizontal lines. Presence of a clot may then be determined if at least one analyte sensor exceeds the threshold, and absence of a clot may be concluded if none of the analyte sensors exceeds the threshold. In addition to the event at about 15 hrs, in FIG. 2 two further events of exceeding the threshold indicated by the horizontal lines at (+/−0.3) are observed between 16 hrs and 18 hrs (at about 17 hrs towards positive values), and between 20 hrs and 22 hrs (at about 21 hrs towards negative values), respectively. In fact, after the first event at about 15 hrs, the analyte signals do not really seem to properly stabilize in a manner as before the event, or in a manner as seen in FIG. 3 throughout the entire period of operation shown. Any measurement performed on a user sample after about 15 hrs would have to be discarded retrospectively.

By using the method of the invention, presence of a clot would be determined already at the first event, and an alarm/error state would be presented to a user of the analyzer. Furthermore, measures for clot removal and/or replacement of the measurement chamber by a new one may be initiated. Thereby, loss of data, loss of time for obtaining useless data, and in particular the loss of valuable samples is successfully avoided. Note also that a flow-based detection, such as by liquid sensors would not report any problem from a point of view of the fluidic behavior during filling and discharge of the measurement chamber 2, whereas the inventive method allows for a very sensitive detection of this type of clot.

In a specific embodiment of the invention the slope used for determining a clot on a specific sensor in a three sensor system (Ca, K, Na) is calculated as follows.

$$Ca_{rinse\_syncSlope} = \left( Ca_{rinse_{syncSlope}} - \frac{K_{rinse_{syncSlope}} + Na_{rinse_{syncSlope}}}{2} \right) * t$$

$$K_{rinse\_syncSlope} = \left( K_{rinse_{syncSlope}} - \frac{Ca_{rinse_{syncSlope}} + Na_{rinse_{syncSlope}}}{2} \right) * t$$

$$Na_{rinse\_syncSlope} = \left( Na_{rinse_{syncSlope}} - \frac{K_{rinse_{SyncSlope}} + Ca_{rinse_{syncSlope}}}{2} \right) * t$$

In a perfect situation where the different sensors would have the exact same response, and there is not clot, and the amount of each analyte in the rinse solution is the same, the result for each of the above equations should be zero. However the sensors do respond different to the rinse solution. Whether the analyzer should flag the result as indicating an error on the sensor, that could imply the sensor being covered by a clot, would thus depend on whether the calculated value is above or below a threshold value. The table below shows the threshold limits in a given set-up.

| Parameter | lo [mV] | Hi [mV] |
|---|---|---|
| $Ca_{rinse\_syncSlope}$ | −0.3 | 0.3 |
| $K_{rinse\_syncSlope}$ | −0.3 | 0.3 |
| $Na_{rinse_{syncSlope}}$ | −0.3 | 0.3 |

The invention claimed is:

1. A method of detecting a clot in a measurement chamber of a liquid sample analyzer, wherein the liquid sample analyzer comprises a first analyte sensor, for measuring a first analyte in a liquid sample, and a second analyte sensor, for measuring a second analyte in the liquid sample in the measurement chamber, the method comprising the steps of:
    (a) at least partly filling the measurement chamber with a known solution having a composition comprising the first analyte at a first pre-determined level, and the second analyte at a second pre-determined level,
    (b) obtaining a first sequence of measurement results by the first analyte sensor, the first sequence of measurement results including at least a first measurement value and a second measurement value of the first analyte, and simultaneously obtaining a second sequence of measurement results by the second analyte sensor, the second sequence of measurement results including at least a first measurement value and a second measurement value of the second analyte;
    (c) determining a first mathematical resultant based on a change of the first sequence of measurement results based on the first and second measurement values of the first sequence of measurement results;
    (d) determining a second mathematical resultant based on a change of the second sequence of measurement results based on the first and second measurement values of the second sequence of measurement results;
    (e) obtaining a difference between the change of the first sequence of measurement results and the change of the second sequence of measurement results, such that the first mathematical resultant being based on the first and second measurement values of the first sequence of measurement results is mathematically analyzed with the second mathematical resultant being based on the first and second measurement values of the second sequence of measurement results; and (f) as a result of the difference obtained, performing either:
    (1) a clot removal procedure, or
    (2) flowing the known solution and/or liquid sample through the measurement chamber.

2. The method according to claim 1, wherein determining each of the changes based on respective first and second measurement values includes determining a respective rate of change, wherein presence of the clot is determined if the difference between the rate of change of the first sequence of measurement results and the change of the second sequence of measurement results is above a threshold.

3. The method according to claim 1, wherein presence of a clot is determined if the difference between the change based on the first and second measurement values of the first sequence of measurement results and the change based on the first and second measurement values of the second sequence of measurement results is above a threshold.

4. The method according to claim 1, wherein absence of a clot is determined if the difference between the change of the first sequence of measurement results and the change of the second sequence of measurement results is below a threshold.

5. The method according to claim 1, wherein the first and second analyte sensors are located at different locations along the measurement chamber.

6. The method according to claim 1, wherein the first and/or second sequence of measurement results are used for maintaining a calibration of the first and/or second analyte sensors for subsequent measurements.

7. The method according claim 1, wherein the first and second analyte sensors are configured to measure one or more physical parameters of the first and second analytes to thereby obtain the respective first measurement values and the second measurement values, wherein the one or more physical parameters includes at least one of: an analyte concentration, a partial pressure of a gas in liquid, or a pH-value.

8. The method according to claim 1, wherein the first and second analyte sensors are adapted for measuring the same type of physical parameters, wherein the first and second analytes are the same.

9. The method according to claim 1, wherein the first and second analyte sensors are adapted for measuring the same type of physical parameters for different analytes, wherein the first and second analytes are different.

10. The method according to claim 1, wherein the first and second analyte sensors are electrochemical sensors, each sensor comprising an ion selective electrode.

11. The method according to claim 1, wherein the first analyte sensor includes an electrochemical sensor, wherein the electrochemical sensor includes an electrode device with a solid state inner reference system.

12. The method according to claim 1, wherein the first and second analyte sensors are optical sensors.

13. The method according to claim 1, wherein the liquid sample analyzer comprises a third analyte sensor, for further determining which of the first and second analyte sensors are affected by a clot in the measurement chamber, to thereby be an affected analyte sensor, by cross comparing a change in measurement results of the affected analyte sensor against a respective change in measurement results of the other analyte sensors, wherein the clot is affecting the affected analyte sensor where the change in measurement results is deviating from a respective change in measurement results of the other analyte sensors.

14. The method of claim 1, the method further including triggering an alarm to indicate a presence of the clot.

15. A liquid sample analyzer adapted for performing a method of clot detection, the liquid sample analyzer comprising:

(a) a measurement chamber with an inlet for feeding a liquid sample to the measurement chamber, and an outlet for discharging the liquid sample from the measurement chamber;
(b) a first analyte sensor;
(c) a second analyte sensor;
(d) a third analyte sensor; each of the second analyte sensor and the third analyte sensor facing the measurement chamber, the first, second, and third analyte sensors each being arranged for measuring an analyte in the liquid sample in the measurement chamber; and
(e) a signal processor configured for:
    (i) obtaining a first sequence of measurement results by the first analyte sensor, the first sequence of measurement results including at least a first measurement value and a second measurement value, obtaining a second sequence of measurement results by the second analyte sensor, the second sequence of measurement results respectively including at least a first measurement value and a second measurement value, and obtaining a third sequence of measurement results by the third analyte sensor, the third sequence of measurement results respectively including at least a first measurement value and a second measurement value,
    (ii) determining a change based on respective first and second measurement values of each of the first, second, and third sequence of measurement results,
    (iii) calculating a first average change using the first and second measurement values of each of the second and third sequence of measurement results,
    (iv) calculating a difference between the change based on the first and second measurement values of the first sequence of measurement results and the calculated first average change, and
    (v) as a result of the calculated difference, performing either:
        (A) a clot removal procedure, or
        (B) further feeding the liquid sample to the measurement chamber.

16. The liquid sample analyzer according to claim 15, wherein the liquid sample analyzer is adapted for measurement of blood parameters in a whole blood sample.

17. The liquid sample analyzer according to claim 15, wherein the first and second analyte sensors are located at different locations along the measurement chamber.

18. A method of detecting a clot in a measurement chamber of a liquid sample analyzer, wherein the liquid sample analyzer comprises a first analyte sensor, a second analyte sensor, and a third analyte sensor, each of the first, second, and third analyte sensors being for measuring an analyte in a liquid sample in the measurement chamber, the method comprising the steps of:

(a) at least partly filling the measurement chamber with a known solution having a composition comprising the analyte at a first pre-determined level;
(b) obtaining a first sequence of measurement results by the first analyte sensor, the first sequence of measurement results including at least a first measurement value and a second measurement value, obtaining a second sequence of measurement results by the second analyte sensor, the second sequence of measurement results respectively including at least a first measurement value and a second measurement value, and obtaining a third sequence of measurement results by the third analyte sensor, the third sequence of measurement results respectively including at least a first measurement value and a second measurement value;

(c) determining a change based on respective first and second measurement values of each of the first, second, and third sequence of measurement results;

(d) calculating a first average change using the first and second measurement values of each of the second and third sequence of measurement results;

(e) calculating a difference between the change based on the first and second measurement values of the first sequence of measurement results and the calculated first average change; and (f) as a result of the calculated difference, performing either:
   (1) a clot removal procedure, or
   (2) flowing the known solution and/or liquid sample through the measurement chamber.

19. The method of claim 18, wherein the analyte is selected from calcium, potassium, and sodium.

20. The method of claim 18, the method further comprising:

(a) calculating a second average change using the first and second measurement values of each of the first and third sequence of measurement results; and (b) comparing the change based on the first and second measurement values of the second sequence of measurement results with the calculated second average change to thereby determine if a clot is present.

* * * * *